(12) United States Patent
Lorenzo et al.

(10) Patent No.: US 11,812,981 B2
(45) Date of Patent: *Nov. 14, 2023

(54) VASCULATURE OBSTRUCTION CAPTURE DEVICE

(71) Applicant: DePuy Synthes Products, Inc., Raynham, MA (US)

(72) Inventors: Juan Lorenzo, Davie, FL (US); Kirk Johnson, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 384 days.

This patent is subject to a terminal disclaimer.

(21) Appl. No.: 17/133,826

(22) Filed: Dec. 24, 2020

(65) Prior Publication Data

US 2021/0113227 A1   Apr. 22, 2021

Related U.S. Application Data

(63) Continuation of application No. 16/007,168, filed on Jun. 13, 2018, now Pat. No. 10,898,216.

(51) Int. Cl.
*A61B 17/221* (2006.01)
*A61B 17/22* (2006.01)

(52) U.S. Cl.
CPC .... *A61B 17/221* (2013.01); *A61B 2017/2212* (2013.01); *A61B 2017/22038* (2013.01)

(58) Field of Classification Search
CPC ... A61B 17/22; A61B 17/221; A61B 17/1204; A61B 17/12022; A61B 17/22031;
(Continued)

(56) References Cited

U.S. PATENT DOCUMENTS 6,066,149 A   5/2000   Samson et al.
6,210,370 B1  4/2001   Chi-Sing et al.
(Continued)

FOREIGN PATENT DOCUMENTS

CN   104159525 A   11/2014
CN   104768479 A   7/2015
(Continued)

OTHER PUBLICATIONS

Extended European Search Report issued in corresponding European Patent Application No. 19 17 9707 dated Aug. 6, 2019.
(Continued)

*Primary Examiner* — Ashley L Fishback
(74) *Attorney, Agent, or Firm* — TROUTMAN PEPPER HAMILTON SANDERS LLP

(57) ABSTRACT

A device for capturing an obstruction in a vasculature can include an expandable braid, an invertible braid, and elongated members such as tubes or wires that can be moved to cause the expandable braid to expand and the invertible braid to form a pocket facing toward the expandable braid to thereby capture the obstruction within the pocket. The expandable braid can form a cap at an open end of the pocket so that the pocket and cap define a cavity in which the obstruction can be confined. The device can also have an expandable framework between the expandable braid and the invertible braid that can engage the obstruction to further secure the obstruction between the expandable braid and invertible braid.

20 Claims, 11 Drawing Sheets

(58) Field of Classification Search
CPC .. A61B 2017/22051; A61B 2017/2212; A61B 2017/2215; A61B 2017/22038; A61B 2017/22047; A61B 2017/22048; A61B 2017/22069; A61B 2017/00358
See application file for complete search history.

(56) References Cited

U.S. PATENT DOCUMENTS

| | | |
|---|---|---|
| 6,391,037 B1 | 5/2002 | Greenhalgh |
| 6,485,502 B2 | 11/2002 | Don Michael et al. |
| 7,214,237 B2 | 5/2007 | Don Michael et al. |
| 8,088,140 B2 | 1/2012 | Ferrera et al. |
| 8,945,172 B2 | 2/2015 | Ferrera et al. |
| 9,232,992 B2 | 1/2016 | Heidner |
| 9,351,749 B2 | 5/2016 | Brady et al. |
| 9,358,022 B2 | 6/2016 | Morsi |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,743,944 B1 | 8/2017 | Bonneau et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2002/0062135 A1 | 5/2002 | Mazzocchi et al. |
| 2002/0072764 A1 | 6/2002 | Sepetka et al. |
| 2005/0038447 A1 | 2/2005 | Huffmaster |
| 2006/0015136 A1 | 1/2006 | Besselink |
| 2006/0064151 A1 | 3/2006 | Guterman |
| 2007/0078481 A1 | 4/2007 | Magnuson |
| 2008/0281350 A1 | 11/2008 | Sepetka |
| 2010/0268265 A1 | 10/2010 | Krolik et al. |
| 2010/0324649 A1 | 12/2010 | Mattsson |
| 2011/0202088 A1 | 8/2011 | Eckhouse et al. |
| 2011/0213403 A1 | 9/2011 | Aboytes |
| 2012/0116443 A1 | 5/2012 | Ferrera et al. |
| 2012/0283768 A1 | 11/2012 | Cox et al. |
| 2013/0184739 A1 | 7/2013 | Brady et al. |
| 2013/0197567 A1 | 8/2013 | Brady et al. |
| 2013/0345739 A1 | 12/2013 | Brady et al. |
| 2014/0135812 A1 | 5/2014 | Divino et al. |
| 2014/0142598 A1 | 5/2014 | Fulton, III |
| 2014/0200607 A1 | 7/2014 | Sepetka et al. |
| 2014/0200608 A1 | 7/2014 | Brady et al. |
| 2014/0249565 A1 | 9/2014 | Laine |
| 2014/0316428 A1 | 10/2014 | Golan |
| 2015/0196744 A1 | 7/2015 | Aboytes |
| 2015/0223829 A1 | 8/2015 | Aboytes |
| 2015/0265299 A1 | 9/2015 | Cooper et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0206344 A1 | 7/2016 | Bruzzi et al. |
| 2016/0354098 A1 | 12/2016 | Martin et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |

(56) References Cited

U.S. PATENT DOCUMENTS

| | | |
|---|---|---|
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| CN | 105208950 A | 12/2015 |
| EP | 1 452 142 A1 | 8/2004 |
| JP | 2001-522639 A | 11/2001 |
| JP | 2009-509719 A | 3/2009 |
| WO | 2010/102307 A1 | 9/2010 |
| WO | WO 2014/055609 A1 | 4/2014 |

OTHER PUBLICATIONS

Communication pursuant to Article 94(3) EPC issued in corresponding European Patent Application No. 19 179 707 dated Aug. 27, 2020.

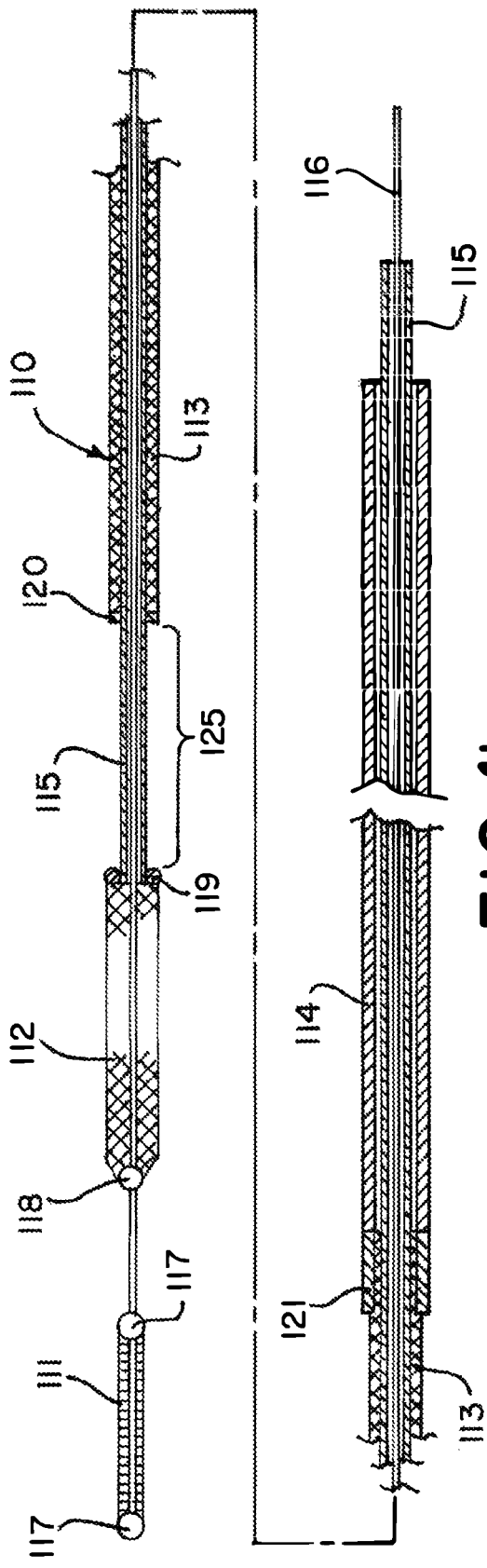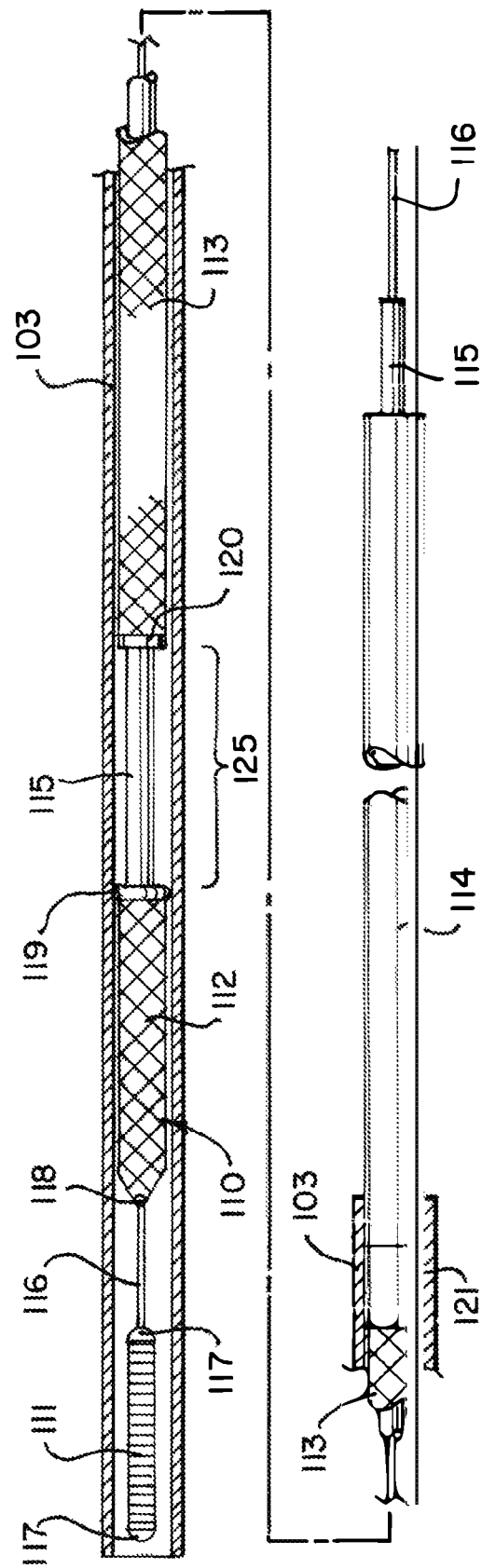

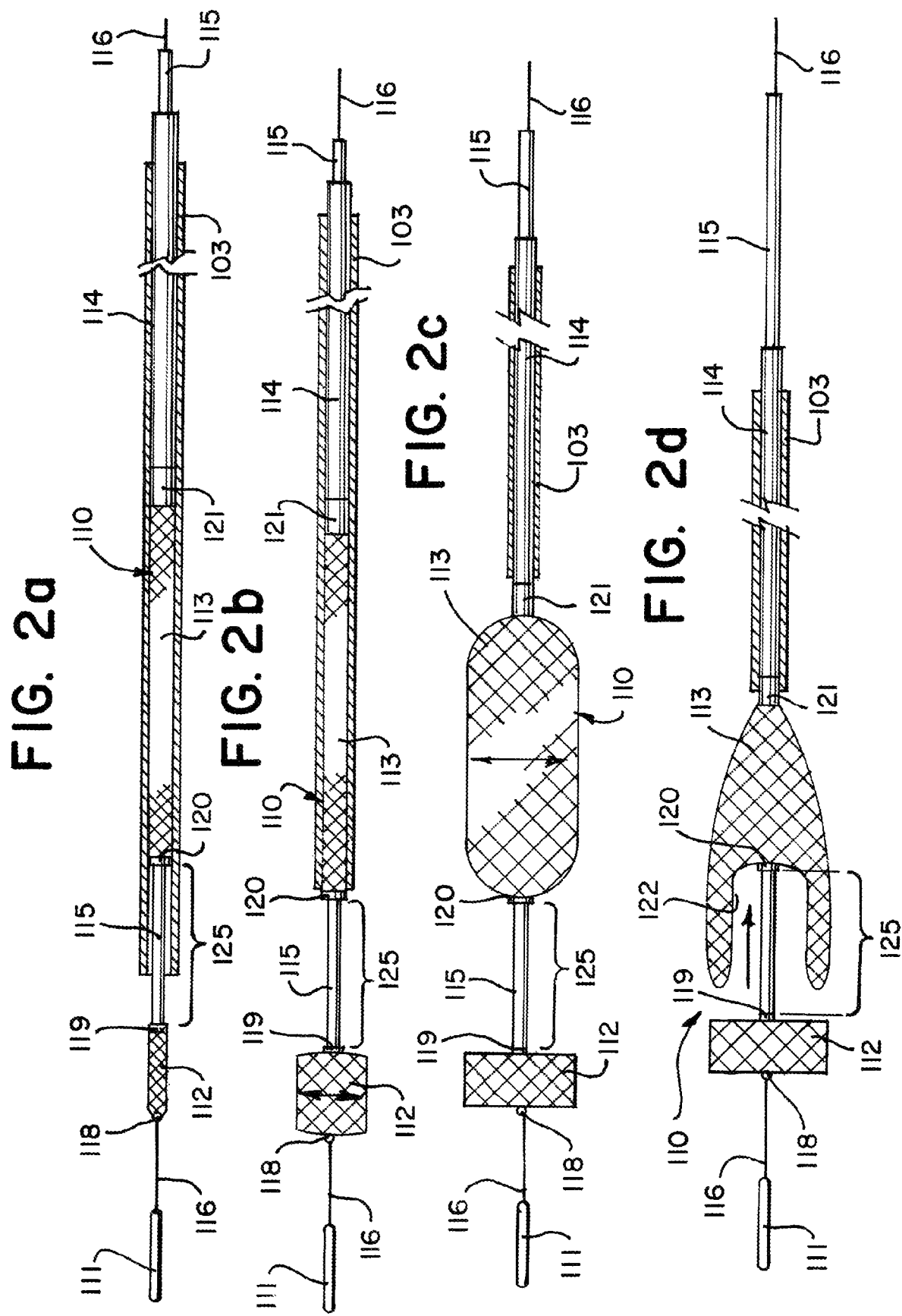

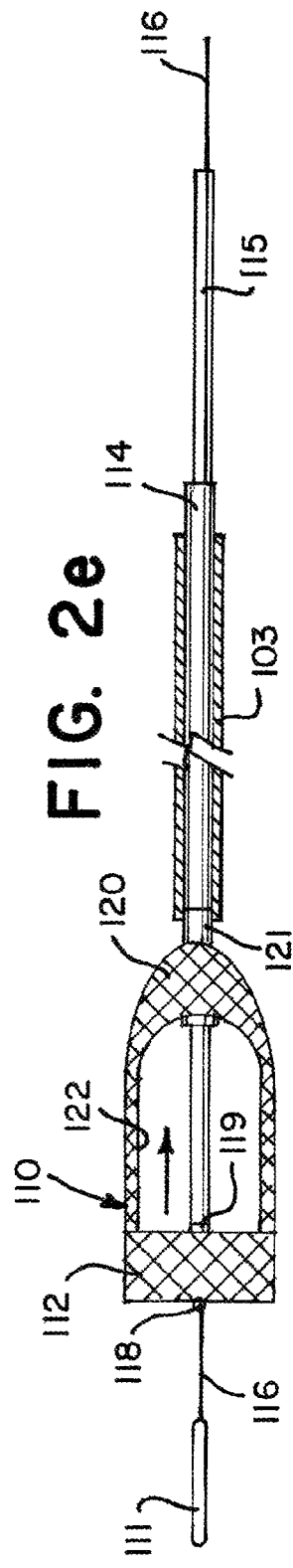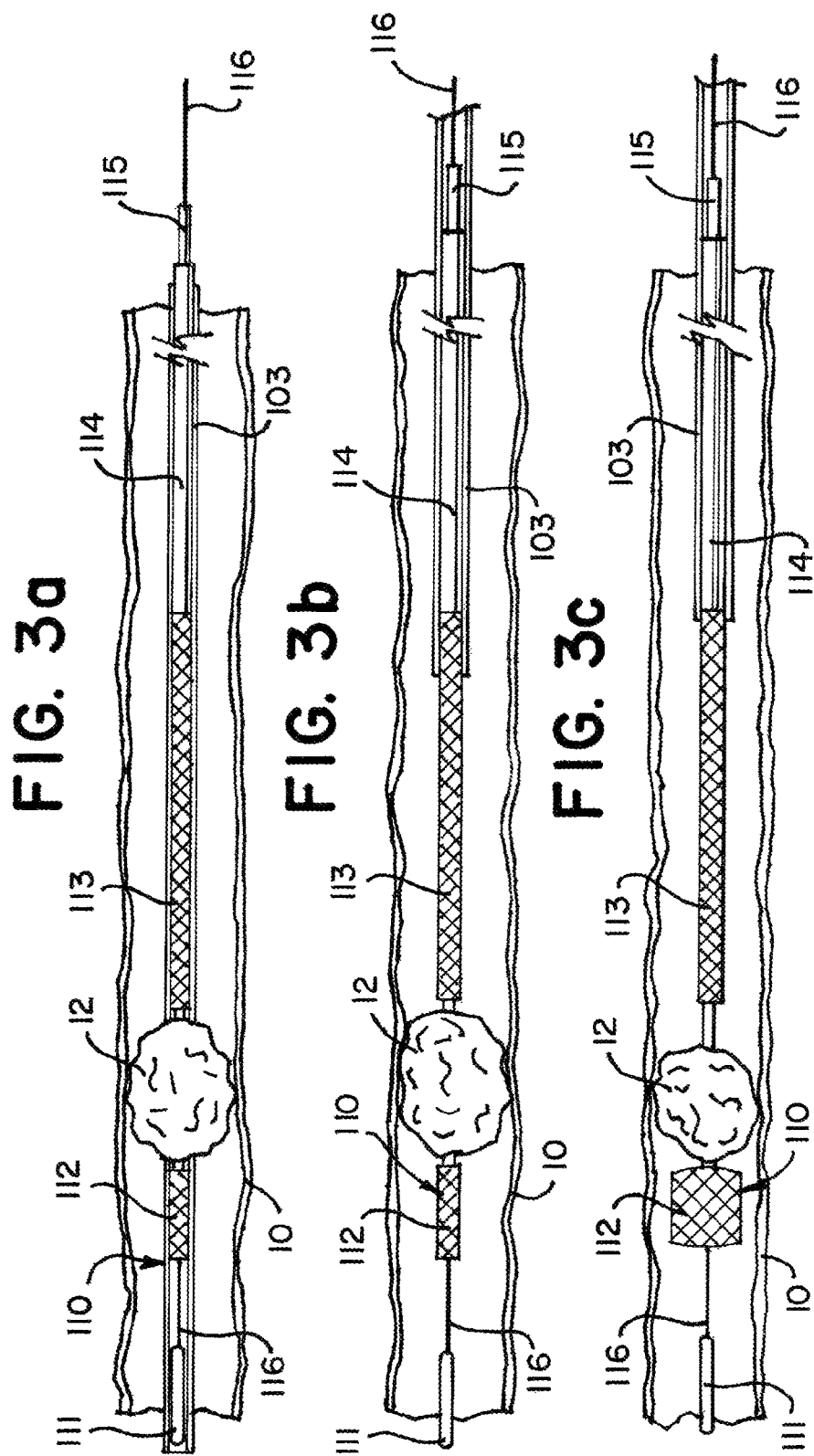

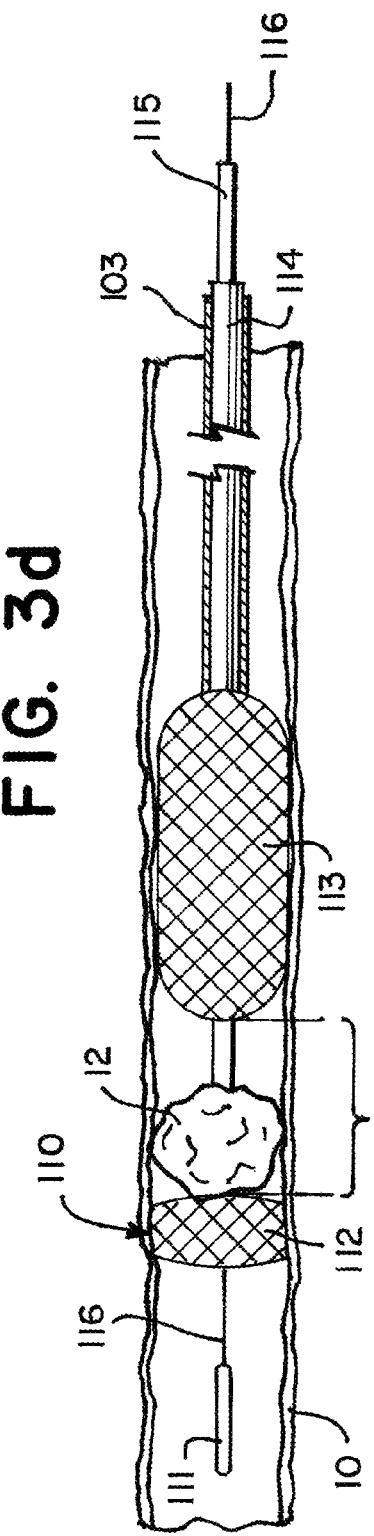
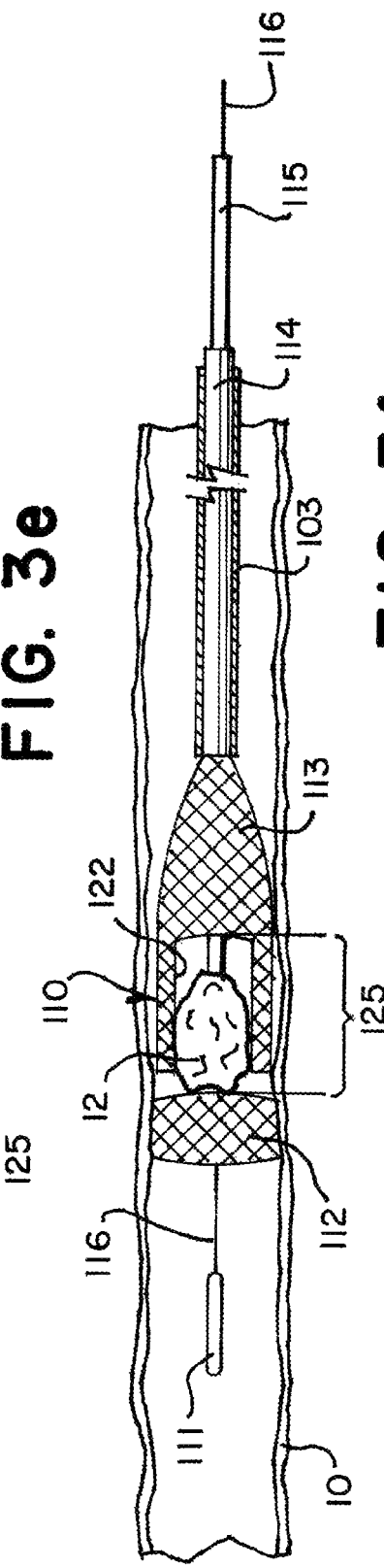
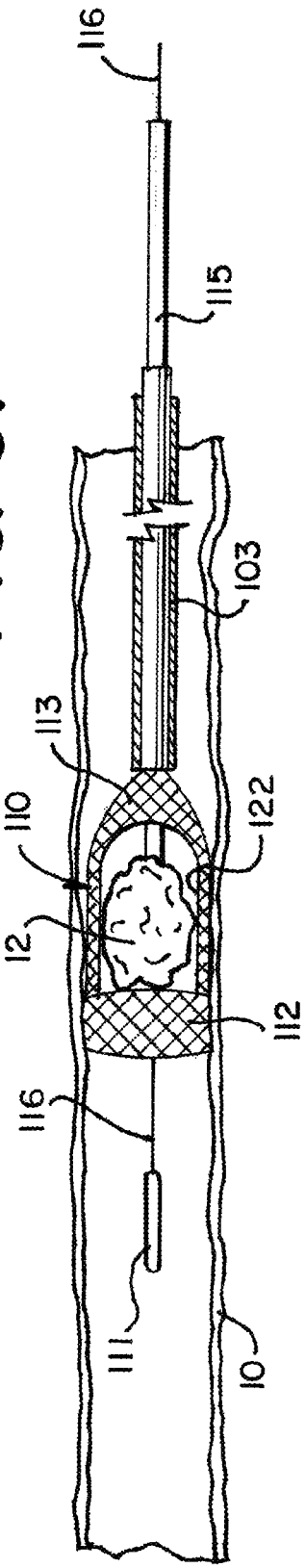

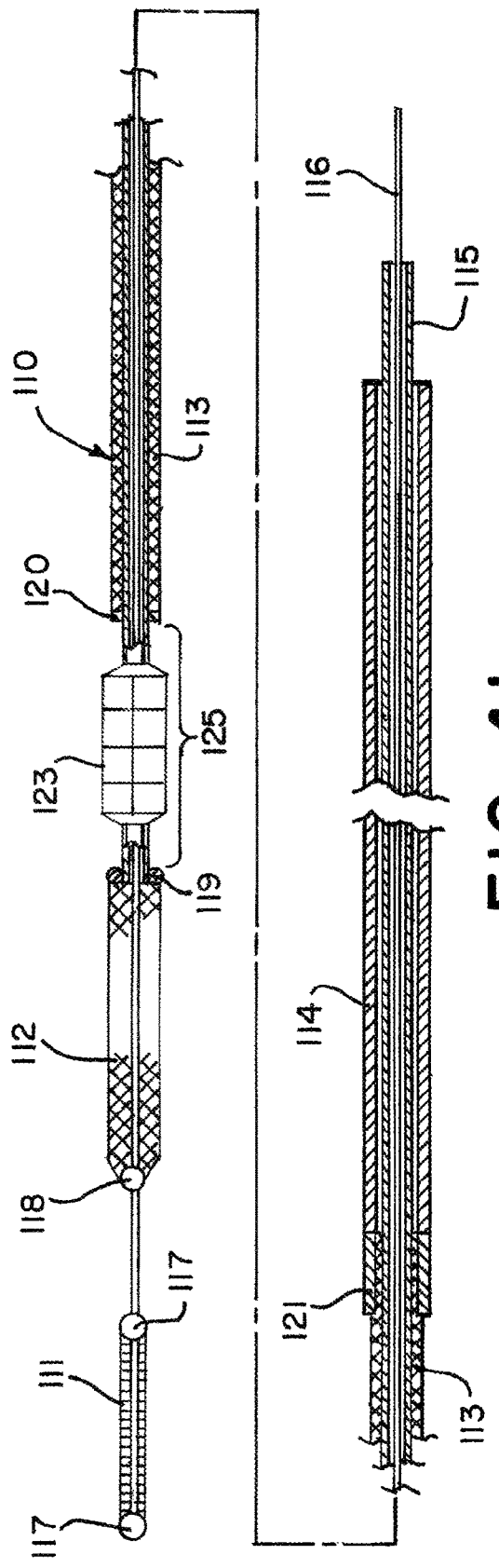
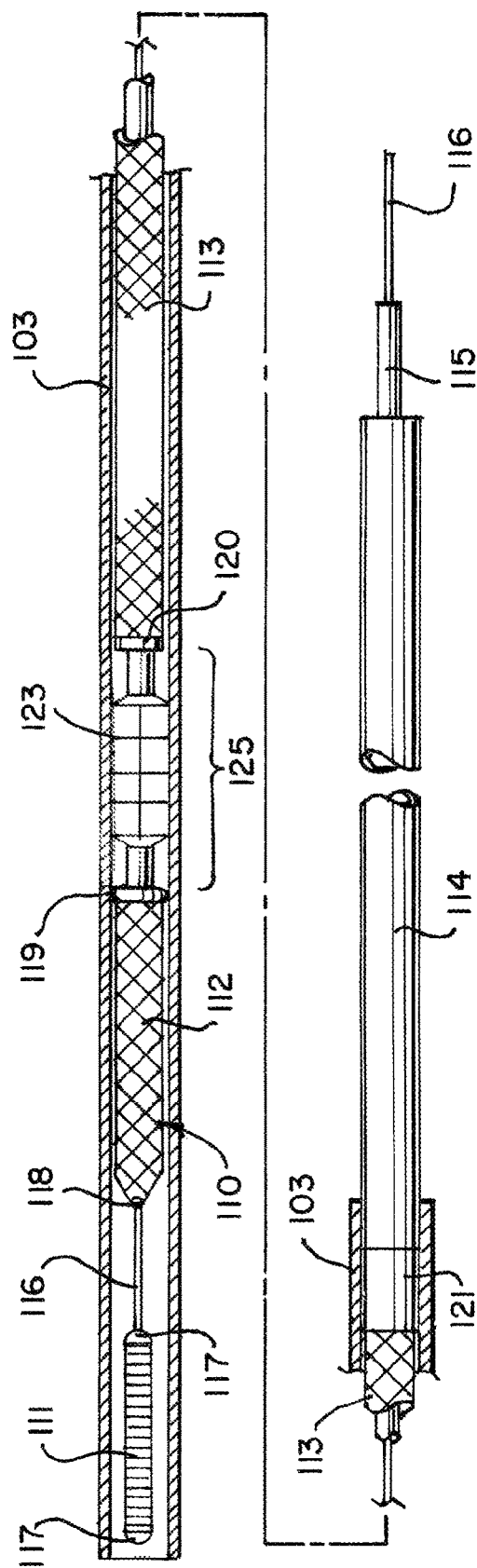

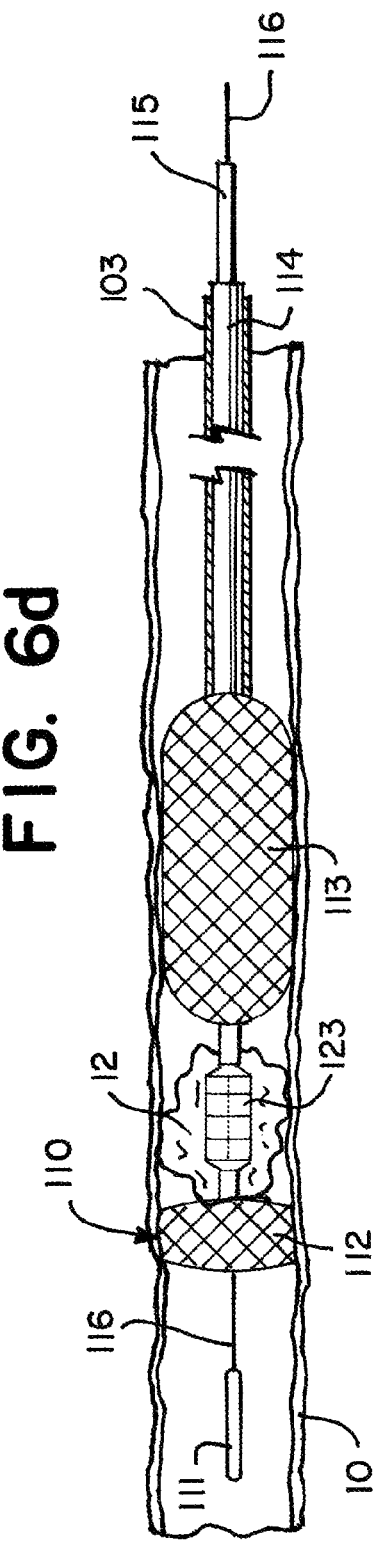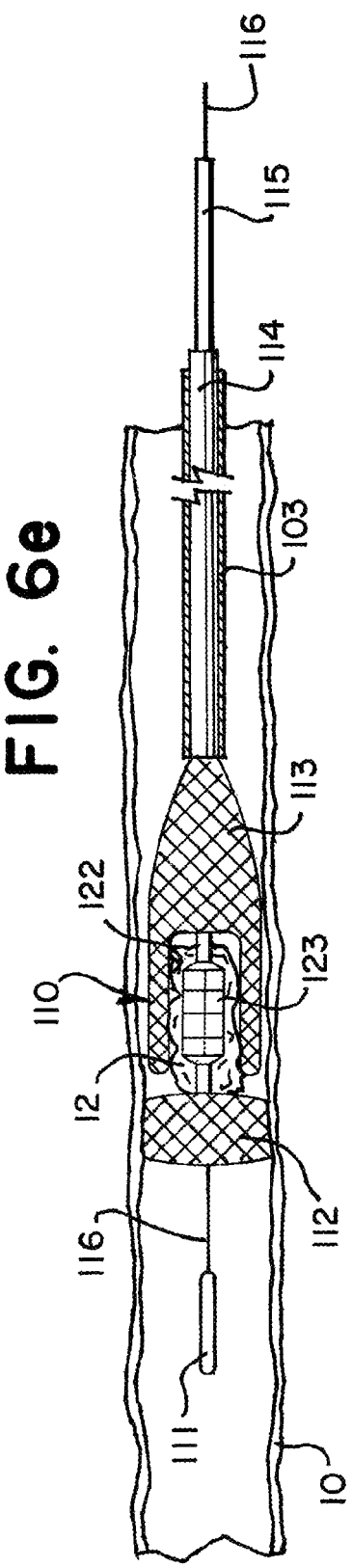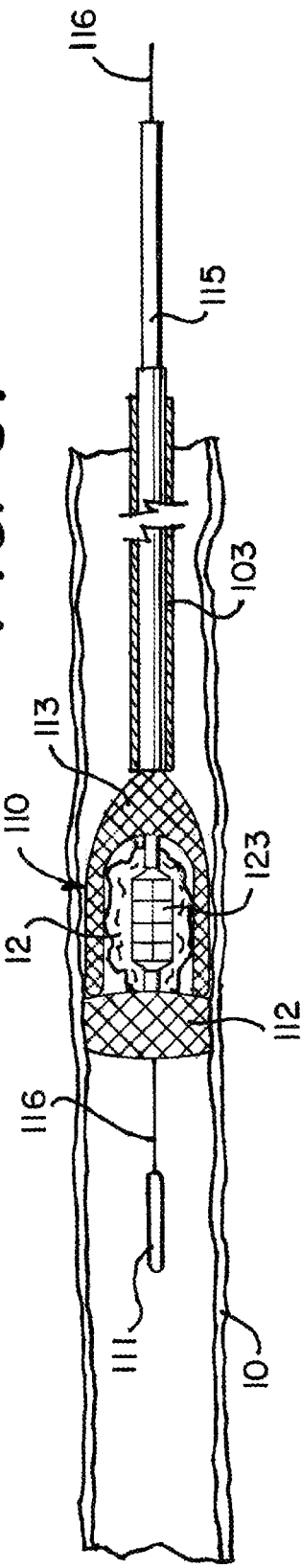

VASCULATURE OBSTRUCTION CAPTURE DEVICE

CROSS-REFERENCE TO RELATED APPLICATIONS

This application is a Continuation of U.S. application Ser. No. 16/007,168 filed on Jun. 13, 2018 which is incorporated herein by reference in its entirety herein into this application as if set forth in full.

FIELD OF INVENTION

The present invention generally relates to medical devices and methods which can be used to remove an obstruction in a blood vessel within a patient, and more particularly, to devices for capturing obstructions in cerebral arteries.

BACKGROUND

Accessing the neurovascular is difficult with conventional technology as the target vessels are small in diameter, are remote relative to the site of insertion, and are highly tortuous compared to blood vessels typically treated by conventional technology. Even though there are over 600,000 acute ischemic strokes in the US each year, clot retrieval devices are used to treat patients in less than <1% of cases. The reasons for this are that conventional technology is either too large in profile, lacks the deliverability to navigate tortuous vessels or is not effective at removing clot when delivered to the target site.

Navigating vessels to approach brain arteries can be difficult due to the aortic arch (especially with in patients with type 2 or type 3 aortic arches), vessel segments having sharp, frequent bends, and the fragility of neurovascular vessels compared to similarly sized vessels in other parts of the body.

Once a device is delivered to the treatment site, the obstruction (e.g. clot, misplaced device, migrated device, large emboli, etc.) can be difficult to dislodge, especially if hours have passed before a patient is catheterized. Pulsing blood pressure and fibrin formation between the obstruction and the vessel wall can strongly adhere the obstruction to the vessel wall. Once dislodged, any portion of the obstruction that is not captured and retrieved can be carried in the direction of blood flow. An ischemic stroke affecting new territory can result if the free obstruction portion lodges elsewhere in the cerebral vasculature.

There therefore exists a need for a vasculature obstruction capture device capable of capturing an obstruction within a cerebral artery for safe retrieval from the patient.

SUMMARY

Disclosed herein are various exemplary devices of the present invention that can address the above needs, the devices generally can include an expandable element, an invertible element, a gap positioned between the expandable element and the invertible element, and an elongated member for delivering the elements to the site of the obstruction. In this manner, the devices permit for an obstruction to be captured within the gap by enveloping the obstruction within a pocket formed by inverting the inverting element.

In one example, the device for capturing an obstruction in a vasculature can include a first elongated member, an expandable element, an invertible element, and a gap. The expandable element and the invertible element can be positioned near the distal end of the first elongated member with a gap in between sized to be placed across the obstruction. The expandable element can expand from a collapsed delivery configuration to an expanded configuration. The invertible element can expand from a collapsed delivery configuration to an expanded configuration, and the invertible element can invert from the expanded configuration to an inverted configuration, thereby forming a pocket. The pocket can envelope at least a portion of the gap and can thereby capture an obstruction that is in the gap.

The expandable element can be positioned distal to the invertible element. The gap can be positioned between a first joint joining the expandable element and the first elongated member and a second joint joining the invertible element and the first elongated member.

The device can include a core wire with a distal coil positioned near the distal end of the core wire. The core wire can be movable in relation to the first elongated member, such that the movement expands the expandable element. The expanded size of the expandable element, or a radius of expansion, can be controlled by the movement of the core wire in relation to the first elongated member.

The device can include a second elongated member movable in relation to the first elongated member, such that the movement expands the invertible element. Moving the first elongated member in relation to the second elongated member can also invert the invertible element. Inverting the invertible element can cause at least a portion of the gap to be enveloped by the pocket formed by inverting the invertible element.

The expandable element and the invertible elements can each be expandable to the walls of the vasculature.

Another example of the device can include a clot engaging element positioned between the expandable element and the invertible element. The expandable element, invertible element, and clot engaging element can each be disposed near the distal end of the first elongated member. The clot engaging element can have a collapsed delivery configuration and can self-expand to an expanded deployed configuration. In the expanded configuration, a portion of the clot engaging element can engage the clot, then upon movement of the clot engaging element, the clot engaging element can pinch the clot in a clot pinching configuration.

At least a portion of the clot engaging element can be enveloped by the invertible element when the invertible element is in the inverted configuration.

The expandable element can be positioned distal the invertible element, and the clot engaging element can be positioned distal the invertible element and proximal the expandable element.

In another example, a method of capturing an obstruction with an obstruction capturing device having a core wire, an expandable element, an invertible element, and a gap positioned between the expandable element and the invertible element can include the steps of providing the obstruction capturing device, placing the gap across the obstruction, expanding the expandable element from a collapsed delivery configuration to an expanded configuration, expanding the invertible element from a collapsed delivery configuration to an expanded configuration, inverting the invertible element from the expanded configuration to an inverted configuration to form a pocket, enveloping at least a portion of the gap by the pocket, and capturing the obstruction in the pocket.

The method can further include enveloping the obstruction within a cavity formed by the pocket and a surface of the expandable element.

The provided device can have a core wire, a first elongated member, and a second elongated member. In this example, the method can further include the steps of moving the core wire relative to the first elongated member to cause the expanding of the expandable element, moving the first elongated member relative to the second elongated member to cause the expanding of the invertible element, moving the first elongated member relative to the second elongated member to cause the inverting of the invertible element, moving the first elongated member relative to the second elongated member to cause the enveloping of the at least a portion of the gap, and moving the first elongated member relative to the second elongated member to cause the capturing of the obstruction in the pocket.

The provided device can have a clot engaging element. In this example the method can include the steps of expanding the clot engaging element from a collapsed delivery configuration to an expanded configuration, thereby engaging the obstruction, and moving the clot engaging element from the expanded configuration to a clot pinching configuration, thereby pinching the obstruction.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 1a and 1b are a cross-sectional side views of an exemplary obstruction capturing device of the present invention;

FIGS. 2a to 2e illustrate configurations of an exemplary obstruction capturing device of the present invention;

FIGS. 3a to 3f illustrate a method of use of an obstruction capturing device of the present invention;

FIGS. 4a and 4b are cross-sectional side views of an exemplary obstruction capturing device of the present invention;

FIGS. 6a to 6f illustrate a method of use of an obstruction capturing device of the present invention;

FIG. 8b is a magnified image of FIG. 8a.

DETAILED DESCRIPTION

Figure 5A:
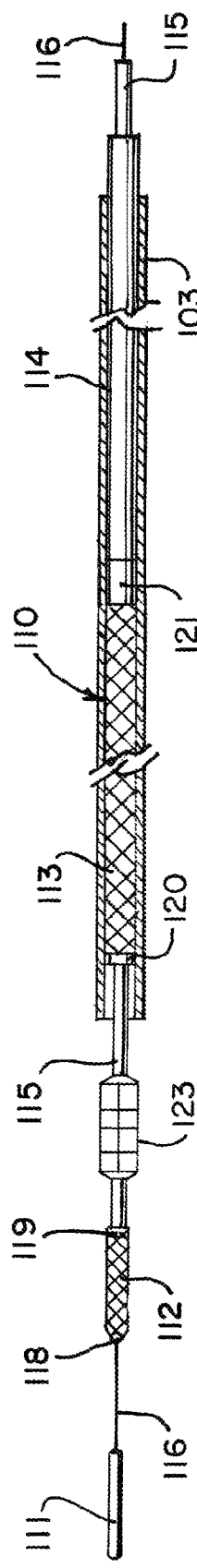
FIGS. 5a to 5e illustrate configurations of an exemplary obstruction capturing device of the present invention.

An example of an obstruction capturing device 110, as illustrated in FIGS. 1a and 1b can have a first elongated member 115, an expandable element 112, an invertible element 113, and a gap 125 positioned between the expandable element 112 and the invertible element 113. As shown, the expandable element 112 can be positioned distal to the invertible element 113 along the first elongated member 115, and the gap 125 can be sized to place across an obstruction. Other geometries, not shown are contemplated. For example, the expandable element 112 can be positioned proximal to the invertible element 113, with the gap 125 positioned between the expandable 112 and invertible element 113.

As shown, the first elongated member can be an inner tube 115 having a lumen therethrough, a proximal end, and a distal end. The inner tube 115 can be connected to the expandable element 112 and the invertible element 113. For example, the inner tube 115 can be joined to the proximal end of the expandable element 112 at a joint 119, the inner tube 115 can be joined to the distal end of the invertible element 113 at a joint 120, and the joints 119, 120 to the inner tube 115 define the gap 125 between the expandable element 112 and the invertible element 113.

The obstruction capturing device 110 can include additional elongated members such as an outer tube 114 and a core wire 116. As shown in FIG. 1a, the core wire 116, inner tube 115, and outer tube 114 can be concentric with the core wire 116 positioned at the axis of tubes, and the inner tube 115 can be positioned inside of the outer tube 114.

The core wire 116 can be connected to a distal coil 111 and the expandable element 112. For example, the core wire 116 can be joined to the distal coil 111 at two joints 117 on the distal and proximal ends of the distal coil 111, and the core wire 116 can be joined to the expandable element 112 at a joint 118 on the distal end of the expandable element 112.

The outer tube 114 can be connected to the invertible element 113. For example, the outer tube 114 can be connected to the proximal end of the invertible element 113 at a joint 121.

As shown in FIGS. 1a and 1b, the expandable element 112 and the invertible element 113 can be in a collapsed delivery configuration. As shown in FIG. 1b, the device 110 can be encased in a catheter 103 such as a microcatheter sized to be placed across an obstruction. For example, the catheter 103 can be sized to puncture an occlusive clot or other embolus.

FIGS. 2a to 2e illustrate configurations of the obstruction capturing device 110. FIG. 2a shows the catheter 103 retracting to expose the expandable element 112. FIG. 2b shows the expandable element 112 expanding from the collapsed delivery configuration to an expanded configuration. As shown in FIG. 2b, the expansion of the expandable element 112 can be accomplished by pulling the core wire 116 proximally in relation to the inner tube 115. In the example illustrated, the expandable element 112 can be joined to the core wire 116 at a distal joint 118 and joined to the inner tube 115 at a proximal joint 119. In such a configuration, pulling the core wire 116 proximally in relation to the inner tube 115 can cause the expandable element 112 to be longitudinally compressed. The longitudinal compression can result in the expandable element 112 expanding radially.

The expandable element 112 can have a flexible structure, such as a mesh, capable of expanding radially when longitudinally compressed or collapsing under longitudinal strain. In such an example, the radius of the expandable element 112 can be controlled by the longitudinal movement of the inner tube 115 in relation to the core wire 116. In certain applications, the radius of expansion can thereby extend to the wall of a vasculature. FIG. 2b also shows the catheter 103 retracted to expose the invertible element 113.

FIG. 2c shows the invertible element 113 expanded from the collapsed delivery configuration into the expanded configuration. FIG. 2c also shows the inner tube 115 pulled proximally in relation to the outer tube 114. In the example illustrated, the invertible element 113 can be joined to the inner tube 115 at a distal joint 120 and joined to the outer tube 114 at a proximal joint 121. In such a configuration, pulling the inner tube 115 in relation to the outer tube 114 can cause the invertible element 113 to be longitudinally compressed. The longitudinal compression can result in the invertible element 113 expanding radially.

FIG. 2c also shows the expandable element 112 maintaining an expanded configuration. In the example illustration, this can be accomplished by pulling the core wire 116 proximally together with the inner tube 115 as the inner tube 115 is pulled proximally. The simultaneous pull can maintain the spacing between the distal and proximal joints 118, 119 of the expandable element 112 connecting the expandable element 112 to the core wire 116 and the inner tube 115 respectively.

FIG. 2d shows the invertible element 113 inverting from the expanded configuration to an inverted configuration. As shown, the inverted configuration can include a concave surface forming a pocket 122. The inversion of the invertible element 113 can be accomplished by continuing to pull the inner tube 115 proximally in relation to the outer tube 114. Pulling the inner tube 115 in relation to the outer tube 114 can cause the invertible element 113 to be further longitudinally compressed. As shown in FIG. 2c and described above, the longitudinal compression can cause the invertible element 113 to expand, however once the invertible element 113 has reached a maximum expansion, further longitudinal compression can cause the invertible element 113 to invert, or fold in on itself as shown in FIG. 2d. During inversion, at least a portion of the gap 125 can be pulled into the pocket 122, becoming enveloped by the invertible element 113.

FIG. 2d shows the gap 125 having a length defined by the distance between the joint 119 between the expandable element 112 and the inner tube 115 and the joint 120 between the invertible element 113 and the inner tube 115. Formation of the pocket 122 can cause the joint 120 between the invertible element 113 and the inner tube 115 to advance into the pocket 122 and the expandable element 112 to advance toward the opening of the pocket 122.

FIG. 2e shows the gap 125 completely enveloped in the pocket 122 of the invertible element 113 and the expandable element 112 butting up against the opening of the pocket 122. The pocket 122 and the adjacent surface of the expandable element 112 can form a cavity.

Other configurations of the obstruction capturing device not shown are contemplated. For example, an invertible element may be positioned distal a proximal element. In such a configuration, the invertible element can be joined to a core wire at a distal joint and jointed to an inner tube at a proximal joint. The expandable element can be joined to the inner tube at a distal joint and joined to an outer tube at a proximal joint. The core wire, inner tube, and outer tube can be elongated members movable by an operator. In such a configuration, moving the outer tube in relation to the inner tube can expand the expandable element, and moving the inner tube in relation to the core wire can expand and invert the invertible element. The invertible element can invert to form a pocket that has an opening that faces proximally. A cavity can be formed within the pocket of the invertible element capped by an adjacent surface of the expandable element. An example method for use of the device in this configuration can include, positioning the gap across an obstruction, pushing the outer tube distally to expand the expandable element, pushing the inner and outer tubes distally to expand and invert the invertible element and envelope the obstruction, moving the microcatheter distally to envelope the device, and extracting the microcatheter from a patient with the device and obstruction contained therein.

The expandable element 112 can be expanded by means not shown. For example, the expandable element 112 can be self-expanding. In such an example, the expandable element 112 can be constrained during delivery by the outer tube 114 or other means and then allowed to expand once the device is positioned to capture the obstruction.

FIGS. 3a to 3f illustrate a method of capturing an obstruction 12 using an obstruction capturing device 110 such as the example devices depicted in FIGS. 1a, 1b, and 2a to 2e.

FIG. 3a shows a device 110 within a vasculature 10, the vasculature 10 containing an obstruction 12 such as an occlusive clot. As illustrated, the device 110 can be contained within the catheter 103. The distal end of the device 110 is delivered through the obstruction 12 and can be positioned such that the gap 125 is placed across the obstruction 12.

FIG. 3b shows the catheter 103 retracted to expose the expandable element 112. As shown, the catheter 103 can be retracted to expose the gap 125 such that it is located through the obstruction 12 and a portion of the invertible element 113.

FIG. 3c shows the expandable element 112 expanding from the collapsed configuration to an expanded configuration, being expanded by moving the core wire 116 in relation to the inner tube 115.

FIG. 3d shows the expandable element 112 expanded radially outward to the walls of the vasculature 10. In this configuration, the expandable element can thereby prevent distal movement of the obstruction 12. FIG. 3d shows the invertible element 113 in the expanded configuration, being expanded by moving the inner tube 115 in relation to the outer tube 114. As shown, the invertible element 113 can be expanded to the walls of the vasculature 10 and can thereby prevent proximal movement of the obstruction 12.

FIG. 3e shows the invertible element 113 in the inverted configuration and the obstruction 12 being moved into the pocket 122 by moving the inner tube 115 in relation to the outer tube 114. As shown, the expandable element 112 can move proximally toward the opening of the pocket 122, pushing the obstruction 12 into the pocket 122 and acting to prevent dislodged portions of the clot 12 from passing farther down the vascular 10 in the blood flow.

FIG. 3f shows the obstruction 12 contained within a cavity formed by the pocket 122 and an adjacent surface of the expandable element 112. The obstruction 12, now captured within the cavity, can be removed from the vasculature 10 by pulling the elongated members proximally. The obstruction 12 can be removed several ways. The device 110 can be reintroduced into the catheter 103 and drawn back encased therein. Alternately, the elongated members can be moved proximately outside the catheter 103. In ether situation, the catheter 103 can be used for aspiration to assure maximum retrieval of all obstruction 12 particles. Further, aspiration may not be necessary, as the combination of the expandable element 112 and the invertible element 113 can assure full obstruction 12 capture.

FIGS. 4a and 4b show an example obstruction capturing device 110 that includes a clot engaging element 123. The clot engaging element 123 can be any clot or embolus capture/stent retriever known to one of skill in the art. For example, see U.S. Patent Application No. 62/536,005, incorporated herein by reference.

As shown in FIG. 4a, the example obstruction capturing device 110 includes the elements described in relation to FIG. 1a including the distal coil 111, expandable element 112, invertible element 113, outer tube 114, inner tube 115, core wire 116, and joints 117, 118, 119, 120, 121. As shown, in FIG. 4a, the clot engaging element 123 can be positioned on the inner tube 115 between the expandable element 112 and the invertible element 113. The clot engaging element 123 can be positioned within the gap 125 to facilitate the capturing of a clot or other embolus (e.g. plaque) 12 within the gap 125.

FIGS. 4a and 4b show the expandable element 112, clot engaging element 123, and the invertible element 113 each in a collapsed delivery configuration. As shown in FIG. 4b, the device 110 can be encased in a catheter 103 such as a microcatheter sized to be placed across an obstruction 12. For example, the catheter 103 can be sized to puncture an occlusive clot or large embolus.

FIGS. 5a to 5e illustrate configurations of the obstruction capturing device 110. FIG. 5a shows the catheter 103 retracted to expose the expandable element 112 and the clot engaging element 123. The clot engaging element 123 can be self-expanding from the collapsed delivery configuration to an expanded configuration, meaning that when not constrained by the catheter 103 or other means, the clot engaging element 123 can expand to the expanded configuration.

Figure 5B:
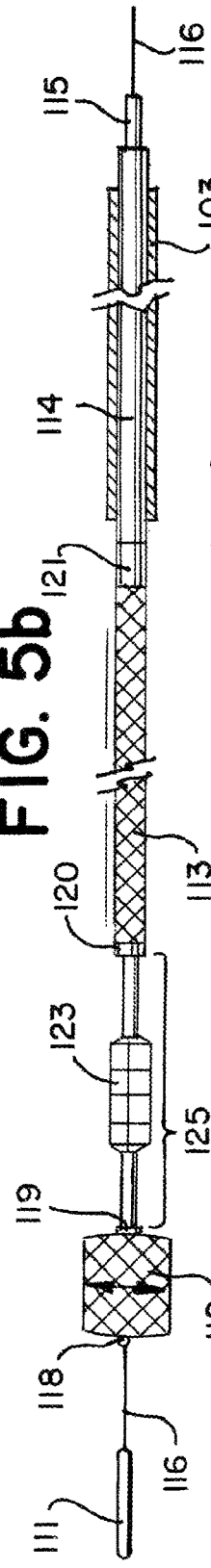

FIG. 5b shows the expandable element 112 expanding from the collapsed delivery configuration to an expanded configuration by pulling the core wire 116 in relation to the inner tube 115, and FIG. 5b shows the catheter 103 retracted to expose the invertible element 113.

Figure 5C:
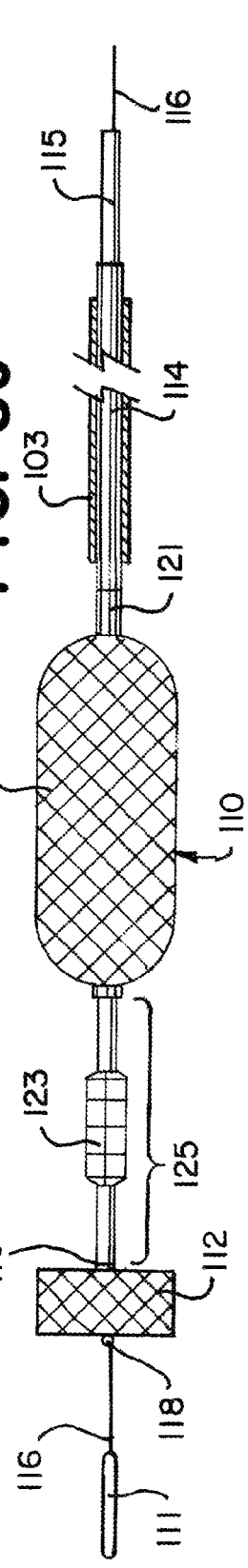

FIG. 5c shows the invertible element 113 expanded from the collapsed delivery configuration into the expanded configuration by pulling the inner tube 115 proximally in relation to the outer tube 114, and FIG. 5c shows the expandable element 112 maintaining an expanded configuration.

Figure 5D:
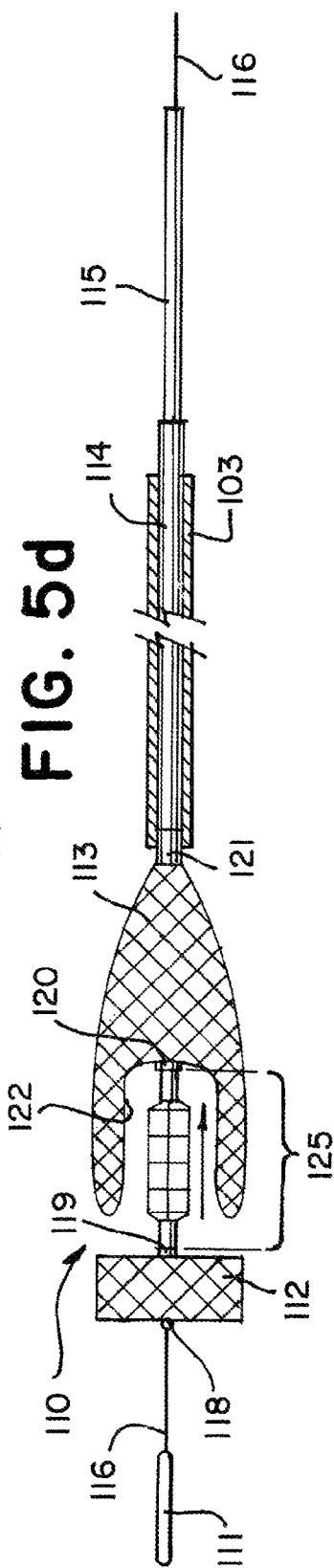

FIG. 5d shows the invertible element 113 inverting from the expanded configuration to an inverted configuration, forming a pocket 122 around the clot engaging element 123. FIG. 5d shows the gap 125 advancing into the pocket 122 and the expandable element 112 advancing toward the opening of the pocket 122.

Figure 5E:
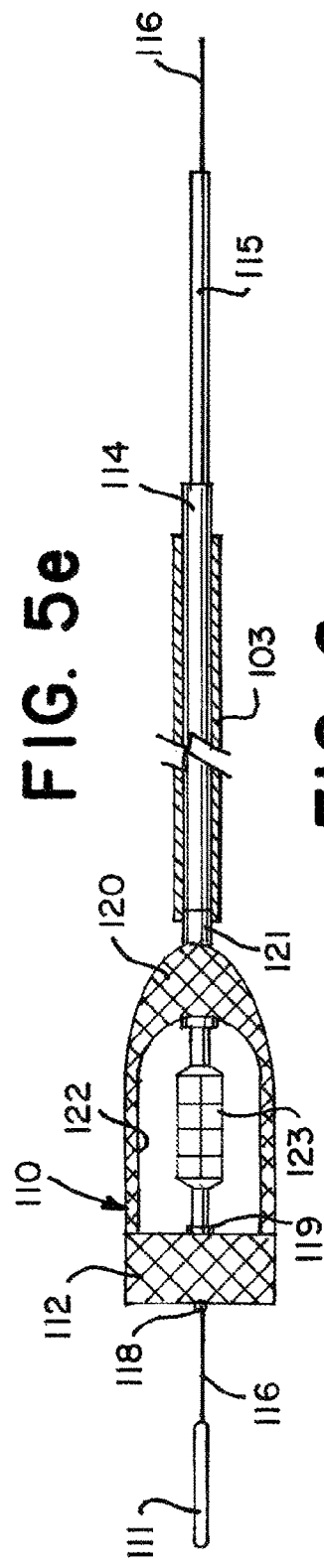

FIG. 5e shows the gap 125 completely enveloped in the pocket 122 of the invertible element 113 and the expandable element 112 butting up against the opening of the pocket 122. The pocket 122 and the adjacent surface of the expandable element 112 forming a cavity.

FIGS. 6a to 6f illustrate a method of capturing an obstruction 12 using an obstruction capturing device 110 such as the example devices depicted in FIGS. 4a, 4b, and 5a to 5e.

Figure 6A:
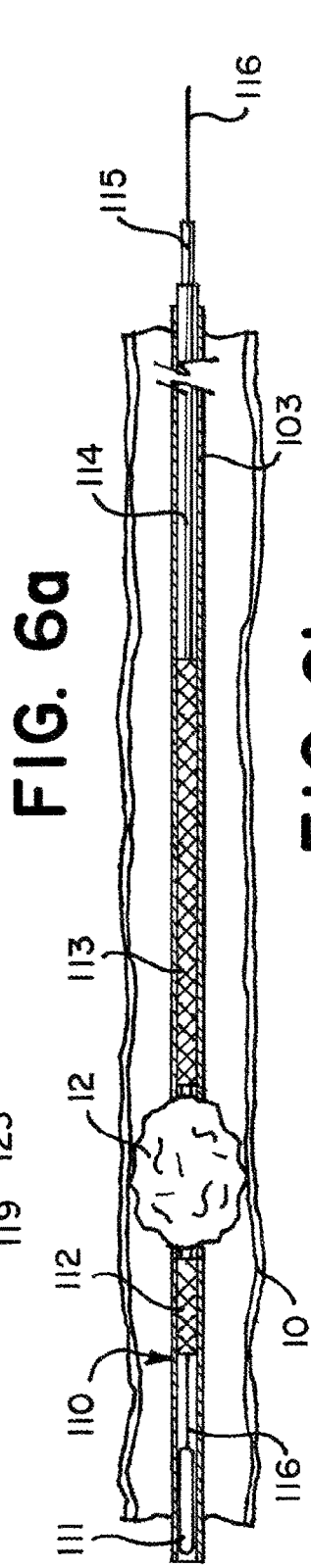

FIG. 6a shows the device 110 contained within the catheter 103 within the vasculature 10, the vasculature 10 containing an obstruction 12 such as an occlusive clot. The device 110 can be positioned such that the clot engaging element 123 and the gap 125 are placed across the obstruction 12.

Figure 6B:
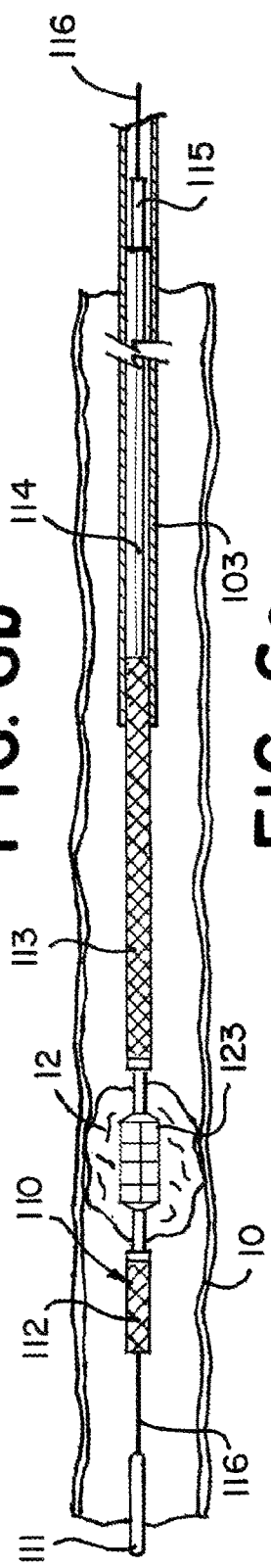

FIG. 6b shows the catheter 103 retracted to expose the expandable element 112 and the clot engaging element 123. In an example application where the obstruction 12 is a clot, the clot engaging element 123 can self-expand within the clot 12 to engage the clot 12.

Figure 6C:
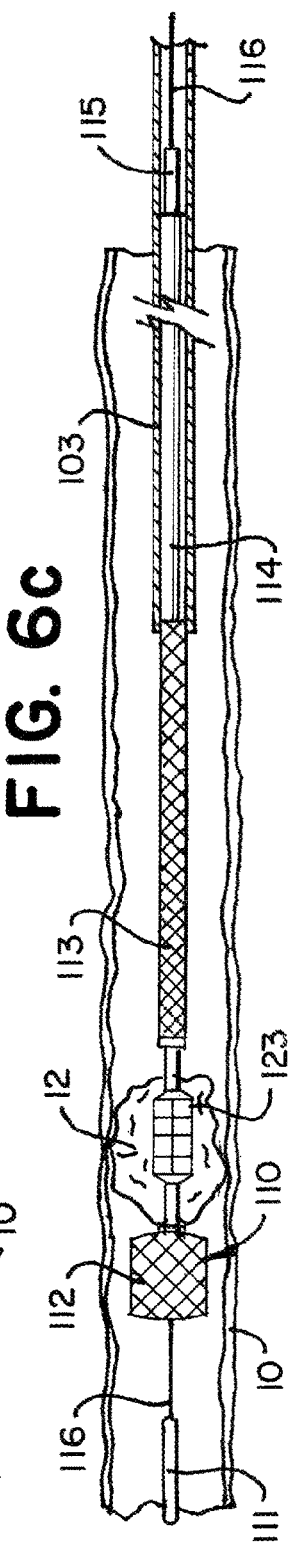

FIG. 6c shows the expandable element 112 expanding from the collapsed configuration to an expanded configuration, being expanded by moving the core wire 116 in relation to the inner tube 115.

FIG. 6d shows the expandable element 112 expanding radially outward to the walls of the vasculature 10. Such a configuration can thereby prevent distal movement of the obstruction 12. FIG. 6d shows the invertible element 113 in the expanded configuration, being expanded by moving the inner tube 115 in relation to the outer tube 114. The invertible element 113 can be expanded to the walls of the vasculature 10 and can thereby prevent proximal movement of the obstruction 12. Pulling the inner tube 115 proximally to expand the invertible element 113 can cause the expandable element 112 and the clot engaging element 123 to move proximally. As the clot engaging element 123 moves proximally, the clot engaging element 123 can pinch the obstruction 12 when moved from the expanded configuration to a clot pinching configuration and can thereby help to dislodge and pull the obstruction 12 proximally. As shown, the expandable element 112 can prevent distal movement beyond the expandable element 112 of any portions of the obstruction 12 not pulled by the clot engaging element 123.

FIG. 6e shows the invertible element 113 inverting to the inverted configuration and the obstruction 12 being moved into the pocket 122 by moving the inner tube 115 in relation to the outer tube 114. The clot engaging element 123 can pull the obstruction 12 proximally while the expandable element 112 can prevent distal movement of the obstruction 12.

FIG. 6f shows the obstruction 12 contained within a cavity formed by the pocket 122 and an adjacent surface of the expandable element 112. The obstruction 12, now captured within the cavity, and can be removed from the vasculature 10 by pulling the elongated members proximally.

Figure 7A:
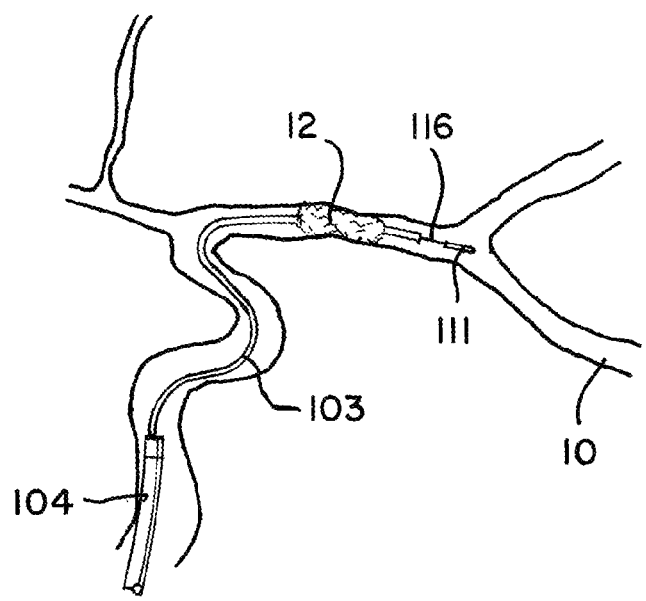
FIGS. 7a to 7e illustrate a method of use of an obstruction capturing device of the present invention.
Figure 7B:
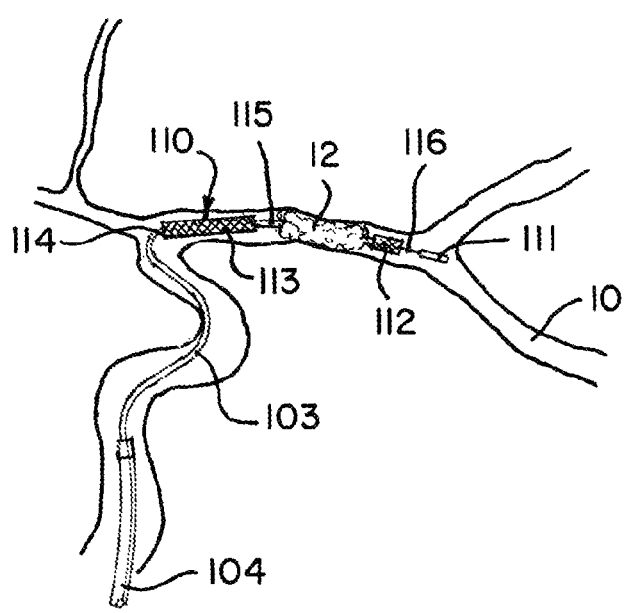
Figure 7C:
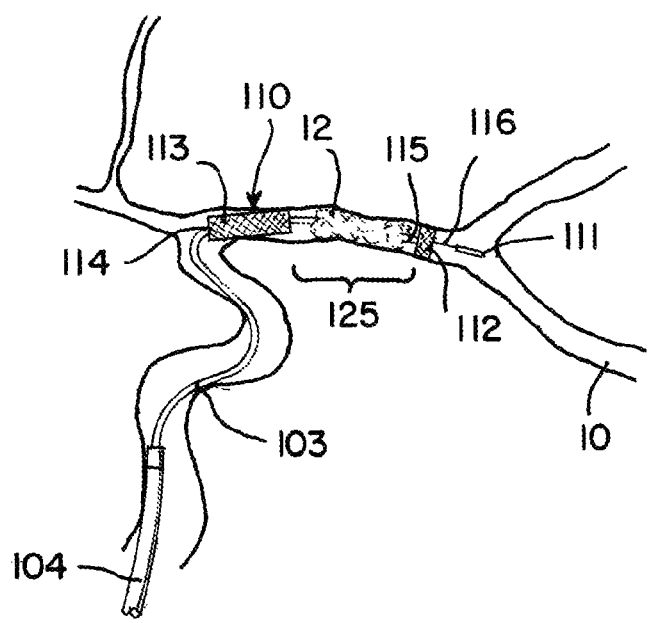
Figure 7D:
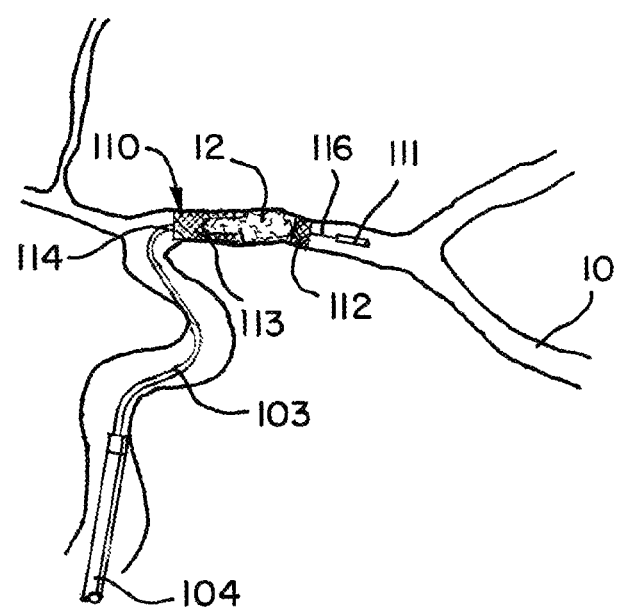
Figure 7E:
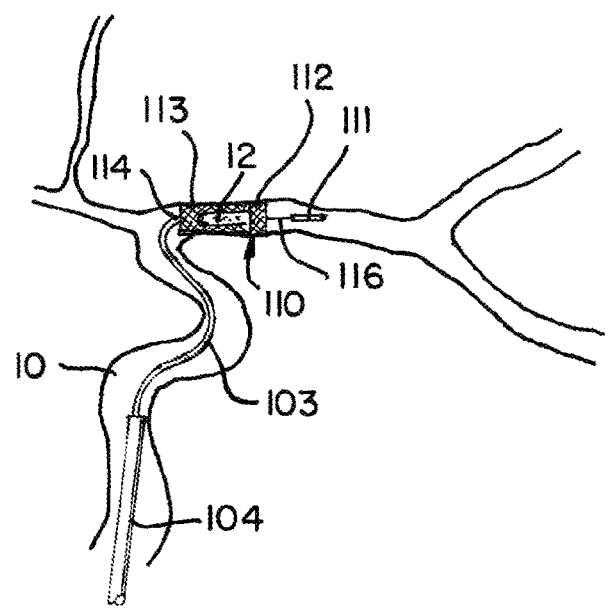

FIGS. 7a to 7e illustrate a method of use of an obstruction capturing device 110 in the context of removing an occlusive clot 12 from a blood vessel 10. FIG. 7a shows the device 110 within a microcatheter 103 penetrated through the clot 12 within the blood vessel 10. As shown, the microcatheter 103 can be delivered to near the treatment site by a guide catheter or intermediate catheter 104. FIG. 7b shows the catheter 103 retracted to expose the expandable element 112 and the invertible element 113, the clot 12 being positioned between the expandable element 112 and the invertible element 113. FIG. 7c shows the expandable element 112 and the invertible element 113 each in an expanded configuration with the clot 12 positioned in the gap 125 between the expandable element 112 and the invertible element 113. FIG. 7d shows the invertible element 113 in an inverted configuration, and the clot 12 being moved into the pocket 122 of the inverted element. FIG. 7e shows the clot 12 being captured within a cavity formed by the pocket 122 of the inverted element and a surface of the expandable element 112.

Figure 8A:
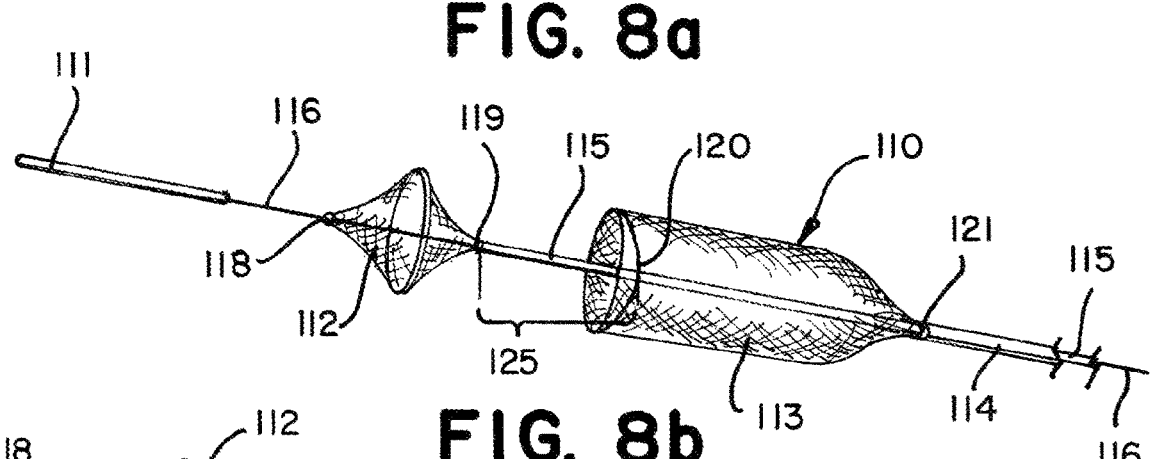
FIG. 8a is an image of a portion of an example manufactured obstruction capturing device according to the present invention.
Figure 8B:
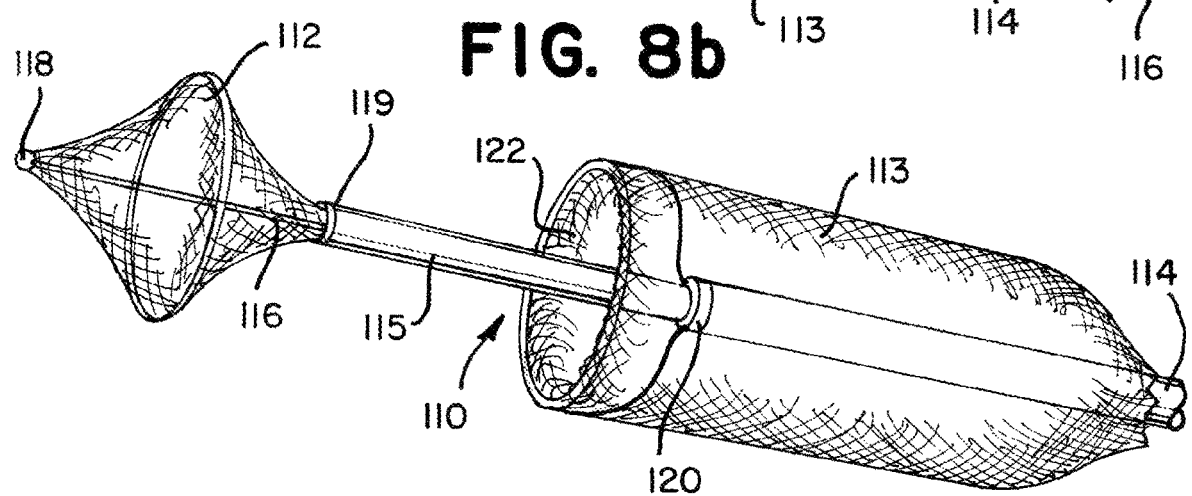

FIGS. 8a and 8b are drawings representing the geometry (to relative scale to each other) of a portion of an example manufactured obstruction capturing device 110. FIG. 8b is a closer view of the device 110 drawn in FIG. 8a.

The descriptions contained herein are examples of embodiments of the invention and are not intended in any way to limit the scope of the invention. As described herein, the invention contemplates many variations and modifications of the obstruction capturing device, including varied relative positioning of the expanding element, inverting element, and clot engaging element, varied configurations utilizing elongated members such as a core wire or concentric tubes, utilizing any of numerous materials for each element or member, incorporation of additional elements or members, utilizing self-expanding elements, or controlling the expansion of elements by moving members for example. These modifications would be apparent to those having ordinary skill in the art to which this invention relates and are intended to be within the scope of the claims which follow.

The invention claimed is:

1. A device for capturing an obstruction in a vasculature comprising:
   a first elongated member comprising a first lumen therethrough;
   a second elongated member comprising a second lumen therethrough, the first elongated member being configured to slide within the second lumen;
   an expandable braid affixed to the first elongated member at a first position, the expandable braid expandable between a collapsed delivery configuration and an expanded configuration; and
   an invertible braid affixed to the first elongated member at a second position in a proximal direction in relation to the first position and affixed to the second elongated member at a third position in a proximal direction in relation to the second position, the invertible braid being expandable between a collapsed delivery configuration and an expanded configuration, the invertible braid being invertible between the expanded configuration and an inverted configuration, the inverted configuration forming a pocket.

2. The device of claim 1, wherein the first position and the second position are a fixed distance from each other.

3. The device of claim 1, wherein a gap sized to place across the obstruction extends between the first position and the second position.

4. The device of claim 1, further comprising a core wire configured to slide within the first lumen, the expandable braid being affixed to the core wire.

5. The device of claim 4, wherein a movement of the core wire in relation to the first elongated member expands the expandable braid.

6. The device of claim 5, wherein the expandable braid comprises a diameter that is expandable and contractible by the movement of the core wire in relation to the first elongated member.

7. The device of claim 1, wherein a first movement of the first elongated member in relation to the second elongated member expands the invertible braid.

8. The device of claim 7, wherein a second movement of the first elongated member in relation to the second elongated member inverts the invertible braid to form a pocket.

9. The device of claim 8, wherein the second movement causes at least a portion the first elongated member between the first position and the second position to be enveloped by the pocket.

10. The device of claim 1, wherein the expandable braid is expandable to walls of a vasculature and the invertible braid is expandable to walls of the vasculature.

11. A device for capturing a clot in a vasculature comprising:
    a first elongated member comprising a proximal end and a distal end;
    an expandable braid positioned near the distal end of the first elongated member, the expandable braid expandable between a collapsed delivery configuration and an expanded configuration;
    an invertible braid, the invertible braid positioned near the distal end of the first elongated member, the invertible braid expandable between a collapsed delivery configuration and an expanded configuration, the invertible braid invertible between the expanded configuration and an inverted configuration; and
    an expandable framework positioned between the expandable braid and the invertible braid.

12. The device of claim 11,
    wherein the expandable framework is positioned on the first elongated member and comprises a collapsed delivery configuration and an expanded configuration, and
    wherein the expandable framework is configured to self-expand from the collapsed delivery configuration to the expanded configuration.

13. The device of claim 12, wherein at least a portion of the expandable framework engages the clot in the expanded configuration and pinches the clot on movement from the expanded configuration to a clot pinching configuration.

14. The device of claim 13, wherein at least a portion of the expandable framework is enveloped by the invertible braid when the invertible braid is in the inverted configuration.

15. The device of claim 11, further comprising a core wire and a second elongated member,
    wherein a movement of the core wire in relation to the first elongated member expands the expandable braid,
    wherein a first movement of the first elongated member in relation to the second elongated member expands the invertible braid, and
    wherein a second movement of the first elongated member in relation to the second elongated member inverts the invertible braid.

16. The device of claim 11, wherein the expandable braid is positioned distal the invertible braid and the expandable framework is positioned distal the invertible braid and proximal the expandable braid.

17. A method of capturing an obstruction from a vasculature comprising the steps of:
    crossing the obstruction with an obstruction capturing device such that an expandable braid of the obstruction capturing device is in distal direction in relation to the obstruction and an invertible braid of the obstruction capturing device is in a proximal direction in relation to the obstruction;
    expanding the expandable braid from a collapsed delivery configuration to an expanded configuration;
    expanding the invertible braid from a collapsed delivery configuration to an expanded configuration by moving a first elongated member to which the expandable braid and the invertible braid are affixed in relation to a second elongated member to which the invertible braid is affixed;
    inverting the invertible braid from the expanded configuration to an inverted configuration to form a pocket by moving the first elongated member in relation to the second elongated member; and
    enveloping at least a portion of the obstruction in the pocket.

18. The method of claim 17, further comprising enveloping the obstruction within a cavity formed by the pocket and a surface of the expandable braid.

19. The method of claim 17, further comprising:
    moving a core wire, to which the expandable braid is affixed, relative to the first elongated member to cause the expanding of the expandable braid; and
    moving the first elongated member relative to the second elongated member to cause the enveloping of the at least a portion of the obstruction in the pocket.

20. The method of claim 17, wherein the obstruction capturing device further comprises an expandable framework, the method further comprising the steps of:
  expanding the expandable framework from a collapsed delivery configuration to an expanded configuration, thereby engaging the obstruction; and
  moving the expandable framework from the expanded configuration to a clot pinching configuration, thereby pinching the obstruction.

* * * * *